United States Patent [19]

Mize et al.

[11] Patent Number: 5,344,952
[45] Date of Patent: Sep. 6, 1994

[54] FLUOROKETONE ENZYME INHIBITORS

[75] Inventors: Patrick D. Mize, Durham; James P. O'Connell, Chapel Hill, both of N.C.

[73] Assignee: Becton, Dickinson and Company, Franklin Lakes, N.J.

[21] Appl. No.: 34,959

[22] Filed: Mar. 22, 1993

Related U.S. Application Data

[62] Division of Ser. No. 282,816, Dec. 12, 1988, abandoned, which is a division of Ser. No. 932,951, Nov. 20, 1986, Pat. No. 4,835,099.

[51] Int. Cl.$^5$ .............................. C07F 9/09; C07F 9/12; C07H 15/04; C07H 15/203
[52] U.S. Cl. ................................ 558/169; 536/17.9; 536/18.4; 558/198; 560/130; 560/253; 560/266
[58] Field of Search ................................ 558/169, 198

Primary Examiner—Robert W. Ramsuer
Assistant Examiner—Michael G. Ambrose
Attorney, Agent, or Firm—Richard E. Brown

[57] ABSTRACT

A method for enzyme immunoassay for a ligand suspected to be present in a liquid sample includes signal amplification by use of at least two enzymes and a blocked modulator for one of the enzymes. Ligand present in the liquid binds to an antiligand and an enzyme-labeled tracer. The resulting bound fraction is separated and the enzyme in the tracer removes the blocking group from the blocked modulator. The modulator activates or inhibits a second enzyme which catalyzes the conversion of a substrate to a product. The presence or absence of the ligand in the liquid is indicated by a signal, such as a color change or a rate of color change, associated with the product. The invention includes a new class of enzyme inhibitors and blocked inhibitors and a kit of materials useful for performing the method of the invention.

3 Claims, 1 Drawing Sheet

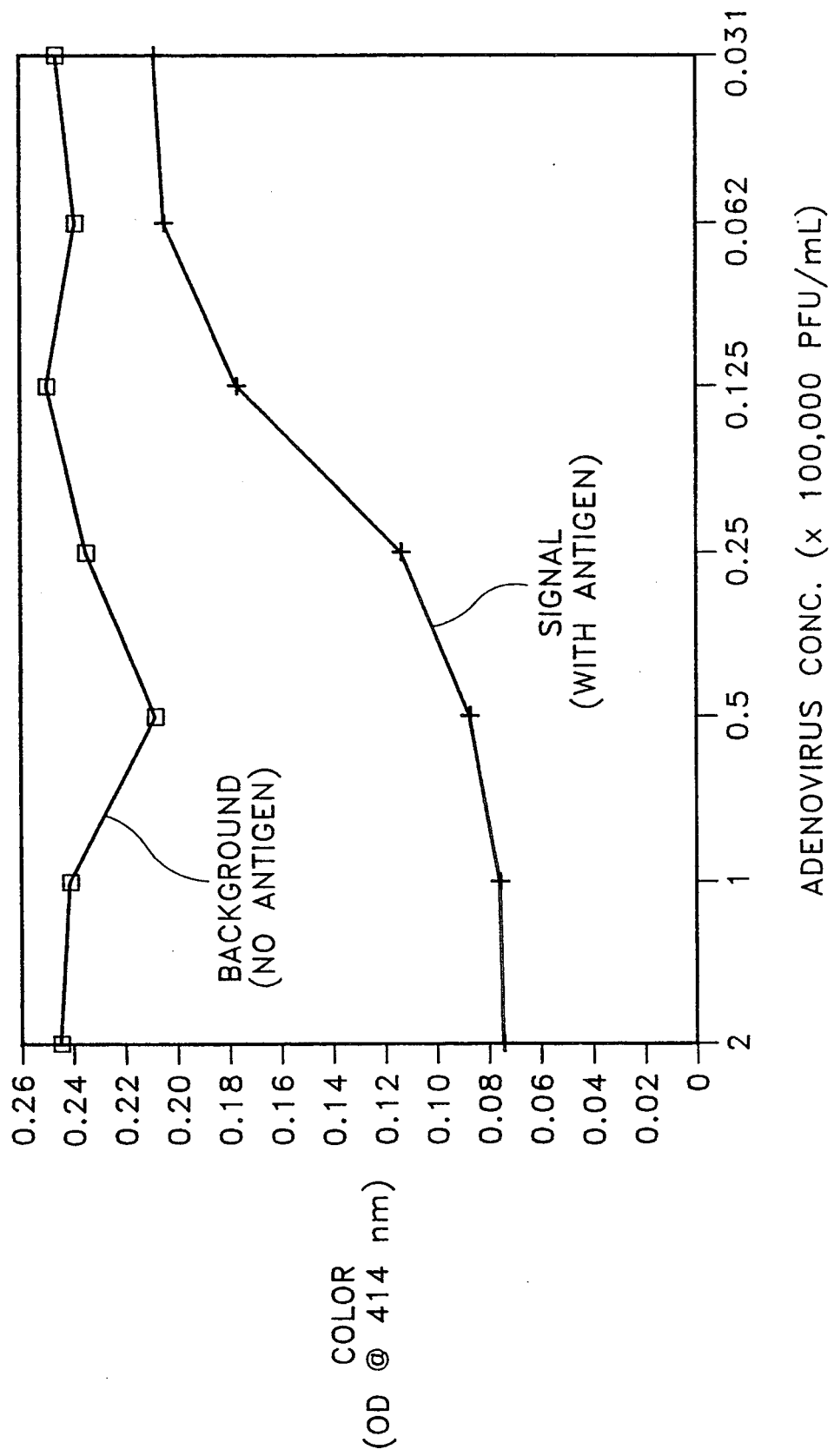

FLUOROKETONE ENZYME INHIBITORS

This is a division of application Ser. No. 07/282,816, filed Dec. 12, 1988, abandoned; which is a division of application Ser. No. 932,951, filed Nov. 20, 1986, now U.S. Pat. No. 4,835,099.

FIELD OF THE INVENTION

This invention relates to immunoassay of an analyte and materials used therein, and more particularly relates to a method and materials for immunoassay in which enhancement of a detectable signal is achieved by modulation of enzymatic catalysis of an indicator reaction.

BACKGROUND OF THE INVENTION

Assay systems which are both rapid and sensitive have been developed to determine the concentration of a substance in a fluid. Immunoassays depend on the binding of an antigen or hapten to a specific antibody and have been particularly useful because they give high levels of specificity and sensitivity. These assays generally employ one of the above reagents in labeled form, the labeled reagent often being referred to as the tracer. Immunoassay procedures may be carried out in solution or on a solid support and may be either heterogeneous, requiring a separation of bound tracer from free (unbound) tracer or homogeneous in which a separation step is not required.

Radioimmunoassay (RIA) procedures use radioisotopes as labels, provide high levels of sensitivity and reproducibility, and are amenable to automation for rapid processing of large numbers of samples. However, isotopes are costly, have relatively short shelf lives, require expensive and complex equipment, and extensive safety measures for their handling and disposal must be followed.

Fluoroimmunoassay (FIA) uses ftuorochromes as labels and provides direct detection of tile label. However, known homogeneous FIA methods using organic fluorochromes, such as fluorescein or rhodamine derivatives, have not achieved the high sensitivity of RIA, largely because of light scattering by impurities suspended in the assay medium and by background fluorescence emission from other fluorescent materials present in the assay medium.

Enzymes have also been used as labels in immunoassay. In conventional enzyme immunoassay (EIA), an enzyme is covalently conjugated with one component of a specifically binding antigen-antibody pair, and the resulting enzyme conjugate is reacted with a substrate to produce a signal which is detected and measured. When the signal is a color change, detection with the naked eye is limited because the average individual can detect the presence of chromophores only down to about $10^{-5}$ or $10^{-6}$ M.

EIA sensitivity carl often be increased by spectrophotometric techniques; however, these procedures require expensive equipment. In another approach, the sensitivity may be increased by various amplification methods. Single enzyme amplification methods have been disclosed in which ligands present at concentrations of $10^{-6}$ to $10^{-10}$ M have been detected. These methods however, have been generally unsatisfactory at ligand concentrations above $10^{-11}$ M. In cascade amplification procedures, the number of detectable (generally colored) molecules is increased by use of two or more enzymes or enzyme derivatives. U.S. Pat. No. 4,463,090 to Harris discloses a cascade amplification immunoassay in which a large molecule activator, such as an enzyme or a proenzyme coupled to a ligand, activates a second enzyme which reacts with a substrate to produce a detectable signal or in turn activates a third enzyme.

U.S. Pat. No. 4,446,231 to Self discloses a cycling amplification enzyme immunoassay which includes primary and secondary enzyme systems and a modulator for the second enzyme system. The primary system includes a first enzyme coupled to a ligand. In a first embodiment of the Self invention, the first enzyme system acts on a modulator precursor to liberate a modulator. The modulator is a cofactor of the secondary enzyme which activates the second enzyme system to catalyze the reaction of a substrate to a detectable product. During the reaction, the modulator is converted to an inactive form, and cycling is accomplished by a third enzyme which reactivates the modulator. In a second embodiment the modulator is an inhibitor of the secondary system, and is removed by the primary enzyme system whereby the secondary system is activated to act on the substrate and thereby produce the detectable product.

Boguslaski et al., U.S. Pat. No. 4,492,751 teaches a cycling system in which an enzyme substrate or coenzyme is conjugated to one member of the specifically binding pair.

A variety of molecules has been shown to cause specific inactivation of a target enzyme. A subset of inhibitors, termed mechanism-based inhibitors, are substrates for enzymes which react with an enzyme to form a covalent bond. Mechanism-based inhibitors have been reviewed by Walsh (Tetrahedron 38, 871 (1982). Another subset of inhibitors includes molecules which act as stable transition-state analogs. Gelb et al. have disclosed some fluoroketones as transition-state inhibitors of hydrolyric enzymes in Biochemistry 24, 1813 (1985).

SUMMARY OF THE INVENTION

One aspect of the present invention is a method for detection of a ligand in a liquid sample, hereinafter referred to as the unknown sample. The unknown sample suspected of containing the ligand is combined with a specific antiligand and a tracer for the ligand. The tracer includes a first enzyme conjugated to either the ligand or to a second antiligand, also specific for the ligand. Conditions conducive to binding between ligand, antiligand and tracer are provided to give a bound phase. After separation of the bound phase from the fluid, the bound phase is contacted in a liquid with a blocked modulator and a second enzyme. The first enzyme removes the blocking group to provide a modulator for the second enzyme. A substrate for the second enzyme is then added. The substrate is converted by the second enzyme to a product which provides a detectable signal, the conversion of the substrate to the product by .the second enzyme being modulated by the modulator.

The ligand may be an antigen, a hapten or an antibody. The preferred ligand is an antigen, most preferably a vital antigen. The method may be carried out by a competitive immunoassay technique, in which case the tracer is the ligand conjugated to the first enzyme. Preferably, a sandwich immunoassay technique may be used, in which case the tracer is a second antiligand conjugated to the first enzyme.

The preferred blocked modulator of the present invention is a blocked inhibitor which is converted by the first enzyme component of the tracer to an inhibitor. The preferred substrate is a chromogen which is convertible by the second enzyme to a product of a different color. Most preferably the chromogen is colorless and is converted to a colored product by the second enzyme, the conversion of chromogen to product being inhibited by the inhibitor.

In the most preferred assay format, an antibody may be affixed to a solid support and contacted under binding conditions with a vital antigen and a second antibody, specific for the antigen, labeled with alkaline phosphatase (first enzyme). After binding and separation, the solid support having an antibody: antigen:alkaline phosphatase-labeled antibody sandwich affixed thereto is contacted with the blocked inhibitor and the second enzyme in a liquid. If antigen is present in the fluid, alkaline phosphatase captured on the solid support removes the blocking group to give the inhibitor. A colorless chromogen is added. Inhibitor generated in the liquid inhibits the second enzyme from converting the chromogen to the -colored product. Thus the development of color indicates the absence of antigen in the sample and failure of color development indicates the presence of antigen in the sample.

In another aspect of the invention, there is provided a new class of enzyme modulators and blocked modulators. The preferred modulators are enzyme inhibitors, most preferably fluoroketones having a functional group to which there is chemically bonded a blocking group which may be cleaved by the first enzyme.

Another aspect of the invention includes a kit of materials for performing the method of the invention substantially as described above.

In any EIA system which includes unblocking of an enzyme inhibitor, severe constraints are placed on both the inhibitor and the blocked inhibitor if the assay is to achieve maximum sensitivity. In accordance with the present invention, the blocked inhibitor is an excellent substrate for the first (unblocking) enzyme, but is essentially unreactive toward the second (color forming) enzyme. Likewise, the unblocked inhibitor is a potent inhibitor of the second enzyme, but has essentially no effect on the first enzyme. Because the reactions of the blocked inhibitor and inhibitor with the first and second enzymes respectively are highly selective, "short circuits" characteristic of prior art cycling EIA systems due to cross reactivities are substantially eliminated.

Thus, the invention provides a versatile method for assay for ligands present in very low concentrations in a fluid. The method makes possible naked eye detection and measurement of an assay signal even though the ligand is present in concentrations as low as $10^{-12}M$ and greatly extends the range of ligands which can be detected or determined without expensive or cumbersome equipment. Further, the assay sensitivity, i.e., time required to detect the presence or absence of the ligand, may be reduced by up to 100 fold compared to conventional EIA. Significant savings in cost and space are thereby achieved, enabling assays in accordance with the invention to be carried out in small clinical laboratories or even in a physician's office.

BRIEF DESCRIPTION OF THE DRAWING

The FIGURE depicts the result of a typical assay in accordance with the method and materials of the Invention.

DETAILED DESCRIPTION OF THE PREFERRED EMBODIMENTS

While this invention is satisfied by embodiments in many different forms, there is described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In accordance with the method of the invention, a substance, hereinafter referred to as the ligand, present in the unknown sample, may be detected visually, i.e., by naked eye observation, even when present in very low concentrations. The method includes at least two amplification stages. A first amplification stage is enzymatic unblocking of a modulator. A second amplification stage is enzymatic catalysis of an indicator reaction. These amplification steps take place sequentially to provide signal amplification of $10^6$ fold or higher whereby a ligand present in the sample at a level of $10^{-12}M$ or lower may be detected with the naked eye. If additional amplification is desired, a first enzyme may be provided which initiates a cascade of sequential reactions involving a plurality of enzymes, wherein any one or all of the reactions may provide further signal amplification.

An immunological reaction is used in the method of the invention for detection of the ligand in the unknown sample. By the term "immunological reaction," as used herein, is meant a specific binding reaction of an antigen and an antibody, a hapten and an antibody, or any appropriate analogue of an antigen, an antibody, or a hapten which also binds specifically.

The immunological reaction may be carried out in any suitable liquid. For example, the liquid may be a body fluid suspected of containing the ligand, such as serum, urine, cerebrospinal fluid, pleural fluid or the like. Alternatively, the liquid may be water, saline or any appropriate buffer, or a mixture of body fluids and other liquids to which has been added a sample suspected of containing ligand.

The preferred method for sandwich assay of the invention will first be described with reference to the assay flow sheet below to provide a general understanding of the assay components and their interaction, after which each component will be discussed in detail.

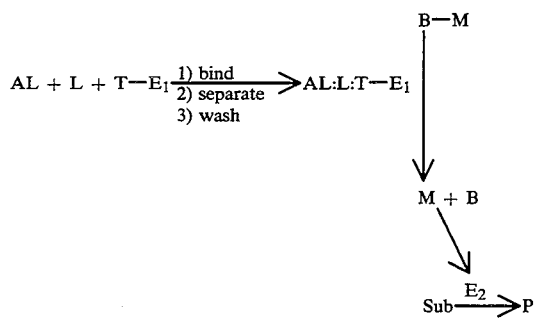

In the above flow sheet, the following definitions apply, wherein a colon indicates an immunological binding, a hyphen indicates a chemical bond or a physical attachment, such as absorption, a solid arrow indicates a chemical conversation and a dotted arrow indicates modulation of a reaction or an assay component.

AL—antiligand
L—ligand
T—tracer
$E_1$—first enzyme
$E_2$—second enzyme
B-M—blocked modulator
M—modulator for enzyme
B—blocking group for modulator
Sub—substrate
P—product It is seen from the flow sheet that conditions conducive to binding of ligand to antiligand and tracer are provided, followed by a separation step and appropriate wash steps. A second enzyme and a blocked modulator consisting of a modulator (activator or inhibitor) and a blocking group are added, and the blocking group is removed by the first enzyme component of the tracer. A substrate for the second enzyme is added, and the conversion of the substrate to a detectable product by the second enzyme is modulated by the modulator liberated from the blocked modulator by the first enzyme. The level of product is either directly or inversely proportional to the level of modulator, and thus to the ligand, depending on whether the modulator is an activator or inhibitor respectively. The actual signal measured may be a color associated with the indicator reaction, as, for example, the color of the product or rate of formation thereof, or the color of the substrate or the rate of disappearance thereof.

In a preferred embodiment of the invention, one or more assay components may be attached to the surface of a solid support. As known in the art, the solid support may be any support which does not substantially interfere with the assay. Exemplary of solid supports which may be used are glass and polymeric materials, such as polyethylene, polyvinylidene fluoride, polystyrene and the like. Such supports may be fabricated into any suitable shape, such as sheets, tubes, wells, or preferably, plates such as microtiter plates. For example, an assay component may be attached to the inside walls and bottom of a tube, preferably a plastic tube with one closed end, or most preferably, to the wells of a microtiter plate. Preferably, after the desired quantity of antiligand is attached to the solid support, any remaining binding sites on the support may be filled by an inert protein. The inert protein may be any protein, as, for example, ovalbumin, which can be attached to the support and which does not interfere in any way with the specific binding reactions between the ligand, antiligand and tracer, as described below.

Preferably, the antiligand attached to the solid support is incubated with ligand and tracer to bind both to the solid support. After a wash step to remove interfering materials, the remaining assay components may be added and the assay carried to completion as described below.

Turning now to a detailed description of the assay components, the ligand may be from any source, and may be an antigen, an antibody or a hapten. For example, the ligand may be an antigen present in a body fluid, or it may be isolated from a body fluid and subsequently introduced into a different liquid, such as buffer. In other cases, the ligand may be from a source other than a body fluid, as, for example, a culture of microorganisms or a cellular extract thereof. Preferred ligands are antigens, most preferably vital antigens present in a body fluid, such as Herpes simplex virus (HSV), Adenovirus, Influenza A virus, parainfluenza 3 virus and Respiratory syncytial virus.

The antiligand is contacted with the ligand in the liquid to induce the immunological reaction. The antiligand may be an antigen or an antibody, either monoclonal or polyclonal, or it may be any appropriate analogue thereof which reacts specifically with the ligand. In addition, the antiligand may be an antibody complex consisting of a plurality of bound antibodies, as, for example, a second antibody bound specifically to a first antibody. Alternatively, the ligand may bind to several different antiligands, for example, an ensemble of polyclonal antibodies or a mixture of several monoclonal antibody molecules which bind simultaneously to different surface areas of the ligand. Generally, the second antibody is raised against the first antibody in a different species. The plurality of bound antibodies in the complex may contain from about two to ten or more antibodies.

In the sandwich assay of the invention, it is preferred to use excess antiligand having sufficient binding sites to bind essentially all of the ligand.

The tracer comprises two components, the first enzyme conjugated to the ligand (competitive assay as described later) or, in the preferred sandwich assay, to a second antiligand. The enzyme may be conjugated to the ligand or antiligand in any suitable way, preferably by a covalent linkage, prior to the immunological reaction. Covalent conjugation of enzymes to ligands or antiligands is conventional and well known to those skilled in the art.

Any enzyme which can remove a blocking group from a blocked modulator may be used as the first enzyme. Suitable first enzymes are generally hydrolases, such as phosphatases, peptidases, esterases, glycosidases and the like. Exemplary of, but not limited to, suitable first enzymes are trypsin, thrombin, mammalian liver esterase, acetylcholinesterase, $\beta$-galactosidase, or most preferably, alkaline phosphatase.

The liquid containing the ligand, the antiligand and the tracer may be incubated, if necessary, to induce binding. Incubation may be carried out at any temperature and for any length of time suitable to facilitate binding, preferably from about 20° to 40° for about 1 minute to 4 hours. Antiligand, ligand and tracer which are bound are hereinafter referred to as the bound fraction and antiligand, ligand and tracer which do not bind are hereinafter referred to as the free fraction. The assay may, but need not, be carried out in such a way that equilibrium is established between the bound and free fractions.

The bound fraction may be separated from the free fraction in the liquid phase of the assay mixture by any conventional method, such as filtration, decantation, centrifugation, aspiration and the like. When the immunological reaction has been carried out on a solid support, the liquid phase is conveniently decanted and the solid support washed to ensure removal of the free fraction and any other materials which would interfere with the assay and resuspended in a suitable liquid such as water, saline or buffer. The blocked modulator is then added, and the pH is adjusted to any level, preferably 6–8, which does not cause non-enzymatic removal of the blocking group, as described below.

The blocked modulator may be any material which may be converted by the first enzyme to a modulator of the second enzyme. The preferred blocked modulator has two components, the modulator and the blocking group. The most preferred blocked modulator is a blocked inhibitor which is unreactive toward the second enzyme until its blocking group is removed by the first enzyme and the inhibitor is liberated into the assay medium. Thus, the choice of the components of the blocked inhibitor depends on the first and second enzymes to be used. The blocking group should be one which can be covalently conjugated to the inhibitor by a bond which can be cleaved substantially selectively by the first enzyme, and the inhibitor component should inhibit the activity of the second enzyme while having substantially no effect on the first enzyme. Thus, the nature of the second enzyme and its substrate will be discussed prior to further description of the blocked inhibitor and the inhibitor.

In the assay of the invention, the second enzyme is generally a hydrolase which converts the substrate to the product. Suitable hydrolases are, for example, phosphatases, peptidases such as trypsin, chymotrypsin and pepsin, or preferably esterases such as acetyl cholinesterase (ACHE) and butyl cholinesterase. The most preferred second enzyme is a carboxyesterase, such as rabbit liver esterase (RLE).

The substrate may be any substance containing a group which can be cleaved by the second enzyme to provide a product detectable by a signal associated with color. Thus, in one embodiment of the invention, the signal detected is the development or disappearance of a color, or a change from one color to another. In another embodiment of the invention, the signal may be a change in the rate at which the substrate is converted to the product, for example, the color of a substrate may be observed to remain unchanged for a specified length of time. Thus, measurements of the signal may be made under either kinetic or thermodynamic conditions. Kinetic measurements determine the rate of change which occurs over a period of time, and are generally carried out by making a series of measurements at various times after combining the assay reagents. Thermodynamic measurements determine the extent of change which has occurred when equilibrium has been reached between the substrate and the product of the indicator reaction. Measurements may be made either instrumentally or, preferably, with the naked eye.

It is preferred that the substrate be colorless until cleaved by the second enzyme to give a colored product. Suitable substrates are indoxyl esters and, preferably, esters of nitrophenols, such as ortho and para nitrophenyl acetates or buryrates. These substrates are colorless until cleavage of the acetyl or butyryl groups by carboxyesterase occurs to give colored nitrophenols. Thus, when the modulator is an inhibitor and the substrate is an ester of a nitrophenol, the signal which is measured is inhibition of color formation.

It is evident that the method of the invention may also be used in a fluorescence immunoassay. In this embodiment of the invention, the second enzyme may convert a nonfluorogenic substrate to a fluorogenic product wherein the signal measured is modulation of fluorescence. For this embodiment of the invention, it is preferred that the modulator be an inhibitor and the second enzyme be an esterase.

As mentioned above, the first enzyme component of the tracer cleaves the blocking group from the blocked inhibitor to provide the inhibitor of the second enzyme, and another aspect of the invention is a new class of enzyme inhibitors and blocked enzyme inhibitors of the general formulas I–IV, set forth below, wherein the nature of group B, as described later, determines whether the compound is an inhibitor or a blocked inhibitor:

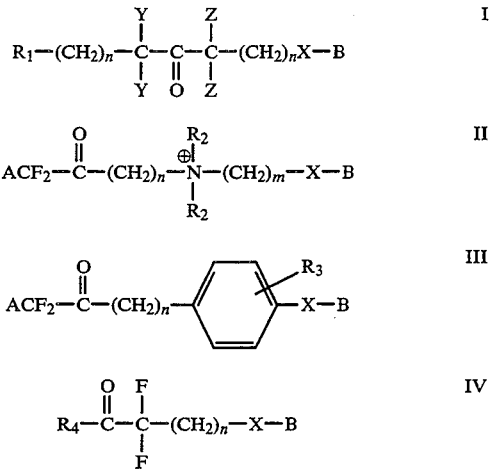

In formulas I–IV, $R_1$ may be H, lower alkyl of 1–6 carbon atoms, branched or unbranched, or

wherein $R_2$ may be lower alkyl of 1–6 carbon atoms; $R_3$ may be H, nitro, alkoxy, halogen and the like; $R_4$ may be an alkyl group of 1–10 carbon atoms or an alkenyl or alkynyl group of 2–10 carbon atoms optionally substituted with an aryl group or an aryl group substituted with a nitro, hydroxyl, mercapto, alkyloxy, haloalkyl, hydroxyalkyl, mercaptoalkyl group; Y and Z may independently be H or F wherein at least one of Y and Z is F; X may be O, S or $NR_5$ wherein $R_5$ may be H or $R_2$; n may be 1–6; m may be 2–6; A may be F or $CF_3$; and B may be H, a phosphoric acid or salt, a glycosyl group, an amino acid residue, such as a lysine or arginine residue covalently conjugated to X through the amino acid carboxyl group, an acyl group of 2–4 carbon atoms such as an acetyl or butyryl group, or a peptide of the formula

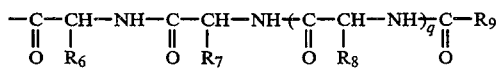

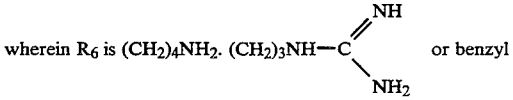

$R_7$ may be H or lower alkyl of 1 to 6 carbon atoms, branched or unbranched; $R_8$ may be H, lower alkyl or hydroxy-lower alkyl of 1 to 4 carbon atoms, branched or unbranched, $CH_2COOH$ or $(CH_2)_2COOH$; $R_9$ may be lower alkyl or lower alkoxy of 1 to 4 carbon atoms, branched or unbranched, phenyl, or benzyloxy; and q may be 0–10.

When B is H, formulas I to IV represent enzyme inhibitors. When B is any group other than H, formulas I to IV represent blocked enzyme inhibitors. When B is a phosphoric acid or salt thereof, it is intended that B have the formula

wherein P is bonded to X and n may be as described above.

The inhibitor and blocked inhibitor in accordance with formulas I to IV may be synthesized by any sequence of conventional chemical reactions as may be envisioned by one skilled in the art. Suitable and convenient methods are given in the Examples, below. The following list of effective enzyme inhibitors is intended to be exemplary only.

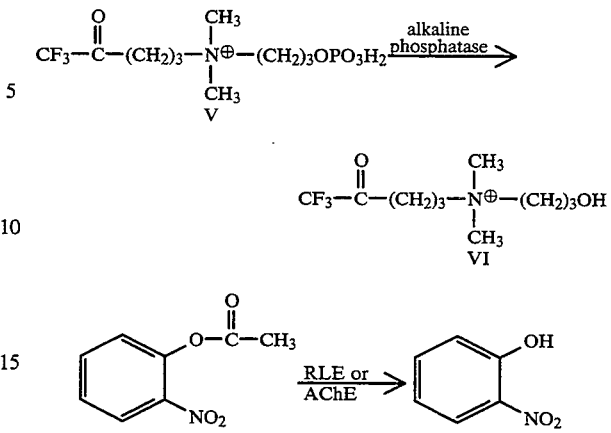

| Name | nmr data | $K_i$ (M) (Esterase) |
|---|---|---|
| 1. 1,1,1-trifluoro-3-(4-hydroxyphenyl)propanone | (CDC13) - 3.91(s, 2H), 5.21(bs, 1H), 6.90(d, 2H), 7.10(d, 2H) | $2.0 \times 10^{-6}$, RLE |
| 2. 1,1,1-trifluoro-3-(3-hydroxyphenyl)-2-propanone | (CDC13) - 4.00(s, 2H), 4.80(bs, 1H), 6.80(m, 3H), 7.30(m, 1H) | $> 10^{-4}$, PLE |
| 3. 1,1,1-trifluoro-4-(4-hydroxyphenyl)-2-butanone | (CDC13) - 2.95(m, 4H), 4.90(bs, 1H), 6.92(dd, 4H)J=4,60Hz | $2.0 \times 10^{-8}$, RLE |
| 4. 1,1,1-trifluoro-4-(3-hydroxyphenyl)-2-butanone | (CDC13) - 2.94(t, 2H), 3.05(t, 2H), 5.70(bs, 1H), 6.80(m, 3H), 7.15(m1H) | $1.0 \times 10^{-7}$, RLE |
| 5. 1,1,1-trifluoro-5-(4-hydroxyphenyl)-2-pentanone | (CDC13) - 1.91(t, 2H), 2.59(t, 2H), 2.68(t, 2H), 5.23(bs, 1H), 6.95(d, 2H), 7.10(d, 2H) | $1.0 \times 10^{-8}$, RLE |
| 6. 1,1,1-trifluoro-5-(3-hydroxyphenyl)-2-pentanone | (CDC13) - 1.95(p, 2H), 2.70(t, 2H), 2.95(t, 2H), 5.40(bs, 1H), 6.70(m, 3H), 7.30(m, 1H) | $1.7 \times 10^{-7}$, RLE |
| 7. 1,1,1-trifluoro-6-(4-hydroxyphenyl)-2-hexanone | (CDC13) - 1.63(m, 4H), 2.59(q, 2H), 2.70(q, 2H), 5.55(bs, 1H), 6.77(d, 2H) 7.02(d, 2H) | $2.0 \times 10^{-8}$, RLE |
| 8. 1-phenyl-3,3-difluoro-10-hydroxy-4-decanone | (CDC13) - 1.35(m, 4H), 1.65(m, 4H), 2.25(m, 2H), 2.70(q, 2H), 2.75(t, 2H), 3.15(bs, 1H), 3.55(t, 2H), 7.25(m, 5H) | — |
| 9. 1,1,1-trifluoro-5-hydroxy-2-pentanone | (CDC13) - 2.15(m, 4H), 4.03(bs, 1H), 4.20(m, 2H) | $3.0 \times 10^{-4}$, PLE |
| 10. 1,1,1-trifluoro-6-hydroxy-2-hexanone | (CDC13) - 1.85(m, 4H), 2.10(bs, 1H), 2.30(m, 4H) | $4.0 \times 10^{-7}$, PLE |
| 11. 1,1,1-trifluoro-8-hydroxy-2-octanone | (CDC13) - 1.30-1.80(m, 8H), 2.40 (bs, 1H), 2.75(t, 2H), 3.65(m, 2H) | — |
| 12. 1-hydroxy-5,5-difluoro-8,8-dimethyl-4-nonanone | (CDC13) - 0.95(s, 9H), 1.45(t, 2H), 2.00(m, 6H), 3.12(bs, 1H), 4.15(m, 2H) | $1.2 \times 10^{-6}$, PLE |
| 13. 1,1,1,2,2-pentafluoro-5-(4-hydroxy-phenyl)-3-pentanone | (CDC13) - 2.94(m, 2H), 3.04(m, 2H), 4.75(bs, 1H), 6.90(d, 2H), 7.10(m, 2H) | $8.0 \times 10^{-7}$, RLE |
| 14. 1,1,1-trifluoro-4-(3-hydroxyphenyl)-3-trans-buten-2-one | (CDC13) - 5.90(bs, 1H), 6.90(d, 1H) j=16HZ, 7.25(m, 4H), 7.95(d, 1H) j=16Hz | $1.6 \times 10^{-7}$, RLE |
| 15. N,N-dimethyl-N-[2-(hydroxy)ethyl] 5,5,5-trifluoro-4-oxopentanaminium, hydroxide salt | (D20) - 1.90(m, 4H), 3.13(s, 6H), 3.30(m, 2H), 3.48(m, 2H), 4.01(bs, 2H). | $5.0 \times 10^{-9}$, AChE |
| 16. N,N-dimethyl-N-[4-(hydroxy)butyl] 5,5,5-trifluoro-4-oxopentanaminium, hydroxide salt | (D20) - 1.95(m, 4H), 2.54(m, 4H) 3.10(s, 6H), 3.35(m, 2H), 3.55(m, 2H), 5.25(bs, 1H) | $6.5 \times 10^{-8}$, ACHE |

PLE, Pig Liver Esterase (E.C. 3.1.1.1)
RLE, Rabbit Liver Esterase (E.C. 3.1.1.1)
AChE, Acetyl Choline Esterase (E.C. 3.1.1.7)

In the most preferred embodiment of the invention, the tracer is a second antiligand having alkaline phosphatase covalently conjugated thereto. After separation and washing of the solid support and resuspension thereof in a suitable assay liquid, RLE or AChE (second enzyme) and the blocked inhibitor of formula V is added. If antigen is present in the unknown fluid, it and the tracer are captured on the support, and the alkaline phosphatase causes cleavage of the phosphate ester bond of V to give inhibitor of formula VI. The assay is completed by addition of o-nitrophenylbutyrate or o-nitrophenylacetate, VII.

If inhibitor VI formed due to the presence of antigen in the unknown fluid, the activity of the esterase is inhibited, and colorless substrate VII is not converted to colored product VIII. If no antigen is present in the unknown fluid, no alkaline phosphatase is captured on the solid support, no inhibitor VI is formed and colored product VIII therefore forms because the esterase is not inhibited.

In this most preferred embodiment of the invention using $1 \times 10^{-12}$M alkaline phosphatase and $3 \times 10^{-9}$M RLE as first and second enzymes respectively, the presence or absence of an antigen in the unknown fluid down to a level of $1\times 10^{-12}$M can be detected in about seven minutes. If antigen is present in the unknown fluid, no color detectable with the naked eye (ca $1\times 10^{-5}$M of product VIII) develops in this time. If no antigen is present, color does develop. In contrast, by conventional immunoassay using first enzyme (alkaline phosphatase) alone, about 104 minutes are required for the enzyme to cleave sufficient phosphorylated nitrophenol to provide detectable color. Thus, the invention represents a 15 fold increase in assay sensitivity using these reagents at these levels.

As mentioned earlier, another embodiment of the invention is a competitive assay wherein the tracer is a predetermined quantity of the ligand conjugated to the first enzyme. In a competitive assay, the quantity of antiligand used is insufficient to bind all of the ligand and tracer present in the assay liquid so that ligand and tracer compete for the limited number of antiligand binding sites. Thus, in a competitive assay, the quantities of ligand and tracer which bind to the antiligand (bound fraction) are inversely proportional to their concentrations in the assay liquid.

If additional signal amplification is desired, a multistage cascade amplification assay may be carried out wherein a plurality of reagents in the assay medium react sequentially leading ultimately to modulator unblocking. In describing this embodiment of the invention, it is convenient to consider the first enzyme described above as a primary enzyme which enzymatically converts a reagent in the assay medium to a secondary enzyme which unblocks the modulator for the above-described second enzyme. Further, the secondary enzyme, or any subsequent enzyme, may react with additional reagents to provide additional enzymes which may continue the cascade of enzymatic reactions until the modulator is unblocked. By proper selection of reagents to be added to the assay medium, any desired number of amplification stages may be carried out.

Amplification occurs in any embodiment of the invention heretofore described because the first enzyme, or any subsequently formed enzyme, and the second enzyme act as true catalysts wherein a single enzyme molecule may act on an essentially unlimited number of blocked modulator or substrate molecules respectively without being consumed. Thus, in theory, one molecule of each enzyme would be sufficient to perform the method of the invention. In practice, determination of the amounts of the enzymes to be added End the number of amplification stages to be used depend on the level of amplification desired and are well within the purview of one of ordinary skill in the art.

It is evident that an almost unlimited number of competitive and sandwich assay configurations which fall within the scope of the invention can be envisioned. Further, the invention provides assay configurations which are suitable for either detection of the ligand or determination of ligand concentration. Ligand concentration may be determined by comparing the magnitude of the signal generated with the unknown sample with the magnitude of the signal measured upon assay of a range of known quantities of the ligand assayed under essentially identical conditions. When the method of the invention is to be used for determination of ligand concentration, it is advantageous to read signal intensity by an appropriate instrument, such as a spectrophotometer, for example, a Beckman DU7 Spectrophotometer, Beckman Instruments, Inc., Irvine, Calif.

In another embodiment of the invention, the second enzyme may be affixed to the solid phase in close proximity to the antiligand. After the immunological reaction by which the ligand and tracer are captured on the solid support, the support is separated from the liquid phase, washed, and tile blocked modulator is added. The first enzyme portion of the tracer reacts with and liberates the modulator for the second enzyme on the support. The substrate for the second enzyme may then be added and the assay completed as previously described.

Another aspect of the invention is a reagent kit or package of materials for performing an assay for a ligand in accordance with the method of the invention. The kit may include one or more antiligands, a first enzyme which may be conjugated to one of the antiligand, or to the ligand, a second enzyme, and a blocked modulator for the second enzyme wherein one of the antiligands may optionally be attached to a solid support. The kit may also include standards for the ligand, as, for example, one or more ligand samples of known concentration, or it may include other reagents, enzyme substrates, or other labeled or unlabeled specific ligands, antiligands or complexes thereof useful in carrying out the assay. It may include solutions, such as saline or buffers. The components of the kit may be supplied in separate containers, as, for example, vials, or two or more of the components may be combined in a single container.

EXPERIMENTAL

Routine Analytical Techniques—Flash Silica gel chromatography was-performed on ICN silica gel 32–63 mesh at 3–7 psi. Analytical TLC was performed on 0.25 mm 5×20 cm aluminum-backed silica gel plates from EM Scientific. Preparative TLC was performed on 2.0 mm 20×20 cm glass-back silica gel plates from EM Scientific. Melting points were performed on a Thomas Hoover capillary melting point apparatus and are uncorrected. NMR spectra were recorded on an IBM WP-200SY spectrophotometer and chemical shifts are reported in ppm relative to trimethylsilane. HPLC was performed on a Waters 510 two pump system with UV detection using one of two solvent systems on a Brownlee AX- 300 7×250 mm column; System A) initial hold for 5 minutes at 30 mM NH4OAc pH 6.5 followed by a linear gradient to 2.0 M NH4OAc over a 30 minute period followed by a hold at 1.0 M NH4OAc for 5 minutes. System B) used an isocratic buffer system of 30 mM NH4OAc pH 6.5 for 40 minutes. Flow rates were 1.0 mL/minute. Gas Chromatography was performed on a H.P. 5840A Gas Chromatograph equipped with a FID and an automatic injector using a 30 M DB-1 Megabore column purchased from J&W Scientific, Inc. GC conditions were as follows; A three minute hold at 100° C. followed by a 10° C./minute gradient to 250° C. followed by a 3.0 minute hold at 250° C. at 16.0 mL/minute flow rate.

Inhibition constants were measured in 50 mM Tris pH=8.0. Enzyme and inhibitor were incubated at ambient temperature for 20 minutes. Substrate for the enzyme was then added and the rate of hydrolysis was followed spectrophotometrically. The substrate for PLE and RLE was o-nitro-phenylbutrate and for AChE was acetyl thiocholine and Ellman's reagent.

EXAMPLE I

Diammonium [4-(3-oxo-4,4,4-trifluorobutyl)phenyl]phosphate

A. Ethyl 3-(4-methoxyphenyl)-2-(1-oxo-2,2,2-trifluoroethyl)propionate

A 1L four neck round bottom flask, fitted with reflux condenser, dropping funnel, argon inlet, and magnetic stirrer was charged with 7.17 g (0.149M) of a 50% oil dispersion of sodium hydride and 300 mL of dry ethyl ether. Nine mL of absolute ethanol was slowly added to the stirring solution. After the evolution of hydrogen stopped, a mixture of 25 g(0.136M) of ethyl 4,4,4-trifluoromethyl acetoacetate and 21.3 g(0.136M) of 4-methoxybenzyl chloride was added over a 1 hour period. The mixture was then heated at reflux overnight. The reaction mixture was then cooled, extracted with water, 1N HCl, dried (anhydrous MgSO4), and solvent removed under reduced pressure. The crude reaction mixture, 33.5 g, was chromatographed on a 60×300 mm silica gel column with a 1:3 ethyl acetate:hexane mixture. Similar fractions were combined and gave 9.0 g (27%) of the desired product as an oil. nmr(CDCl3) - L 2.12(m,3H), 2.67(m,2H), 3.85(m,3H), 3.90(S,3H), 7.24(q,4H).

B. 1,1,1-Trifluoro-4-(4-hydroxyphenyl)-2-butanone

A 100 mL round bottom flask, fitted with reflux condenser, magnetic stirrer and argon inlet was charged with 2.05 g(6.7mM) of ethyl 3-(4-methoxyphenyl)-2-(1-oxo-2,2,2-trifluoroethyl)propionate, 20 mL of 31% HBr in AcOH, and 10 mL of water. This mixture was heated overnight at 120° C., concentrated under reduced pressure and partitioned between dichloromethane and water. The organic layer was extracted with aqueous bisulfite, saturated sodium bicarbonate, dried (anhydrous MgSO4), and the solvent removed under reduced pressure. The crude reaction mixture was chromatographed on a 50×300 mm silica gel column with 1:1 ethyl acetate:hexane. Similar fractions were combined and solvent was removed under reduced pressure to yield 600 mg(41%) as a clear oil. nmr(CDCl3) - L 2.95(m,4H), 4.90(bs,1H), 6.93(dd,4H)J=4,60Hz.

C. Diethyl [4-(3-oxo-4,4,4-trifluorobutyl)phenyl] phosphate

A 10 mL one neck round bottom flask, fitted with argon inlet and magnetic stirrer was placed in an ice bath and charged with 400 mg(1.8 mM) of 1,1,1-trifluoro-4-(4-hydroxyphenyl)-2-butanone, 400 mg(2.4 mM) of diethyl chlorophosphate, 0.15 mL of dry pyridine and 5 mL of dichloromethane at 5° C. The mixture was stirred overnight at ambient temperature, filtered to remove pyridine HCl, extracted with 0.2N HCl, extracted with water, and dried (anhydrous MgSO4). Solvent removal under reduced pressure gave a crude yield of 600 mg of a brown oil. Preparative TLC using 1:1 ethyl acetate:hexane gave 600 mg(92%) of a clear oil nmr(CDCl3) - L 1.50(m,6H), 3.0(m,4H), 4.20(m,4H), 7.15(s,4H).

D. Diammonium [4-(3-oxo-4,4,4-trifluorobutyl)phenyl] phosphate

A 25 mL one neck round bottom flask, fitted with argon inlet and magnetic stirrer was charged with 5.0 mL of dichloromethane, 140mg(0.4 mM) of diethyl [4-(3-oxo-4,4,4-trifluorobutyl)phenyl] phosphate and 2.0 mL of bromotrimethylsilane. After stirring this mixture for 3 hours at ambient temperature, 10 mL of methanol was added and the volatile materials were removed under reduced pressure. The residue was dissolved in water and the pH adjusted to 7.3 with 1.0 N NaOH. The aqueous solution was extracted with ethyl ether and lyophilized to give 190 mg of a white solid. This material was dissolved in 10 mL of 30 mM NH4OAc buffer and purified by HPLC using system A. Yield of the product after lyophilization was 50 mg (37%). mp 235°–240° C. nmr(D2O) -L 1.90(m,2H), 2.56(m,2H), 4.65(s,DOH), 6.88(dd,4H)J=6, 82 Hz.

EXAMPLE II

1-Hydroxy-5,5-difluoro-8,8-dimethyl-4-nonanone

A. Ethyl 2,2-difluoro-5,5-dimethylhexanoate

A 100 mL three neck round bottom flask fitted with dropping funnel, argon inlet, ice bath, and magnetic stirrer was charged with 8.0 mL of dichloromethane and 2.21 g(20 mM) of ethyl 2-oxo-5,5-dimethylhexanoate. Diethylaminosulfur trifluoride, 2.11 g(13 mM), in 5 ml of dichloromethane was added to the reaction mixture over a 15 minute period and the mixture was stirred overnight at ambient temperature. The reaction mixture was partitioned between water and dichloromethane, the organic layer dried (anhydrous MgSO4), and the solvent removed under reduced pressure. The oily residue was distilled at 83°–88° C. at 20 mm to give 1.0 g(25%). nmr(CDCl3) -L 0.95(s.9H), 1.40(m,.4H), 2.10(m,2H), 4.35(q,2H).

B. 2,3,4,5-Tetrahydro-2-oxo-3-[(5,5-dimethyl-2,2-difluoro-1-oxo)hexyl]furan A 25 mL three neck round bottom flask, fitted with drying tube, dropping funnel, heating mantle, and magnetic stirrer was charged with 0.24 g(5.0 mM) of sodium hydride in a 50% oil dispersion. The sodium hydride was washed with dry hexane (2×10 mL) and 5.0 mL of ethyl ether was added to the flask. A mixture of 5 drops of absolute ethanol and 5 mL of ether was slowly added to the sodium hydride suspension. After the evolution of hydrogen had stopped, a mixture of 1.0 g(5.0 mM) of ethyl 2,2-difluoro-5,5-dimethylhexanoate and 0.43 g(5.0 mM) of γ-butyrolactone in 5.0 mL of ethyl ether was added over a 20 minute period. The solution was refluxed for 3 hours and allowed to stir at ambient temperature overnight. The reaction mixture was partitioned with 1N HCL, the organic layer washed with water (2×50 mL), dried (anhydrous MgSO4), and the solvent removed under reduced pressure. The oily residue, 0.88 g, was crystallized from a hexane:ethyl acetate mixture, 0.66 g (53%). nmr - (CDCl3) -L 0.95(s,9H), 1.35(m,2H), 2.00(m,3H), 2.50(m,2H), 3.00(mlH), 4.25(m,1H), 4.5(m,1H).

C. 1-Hydroxy-5,5-difluoro-8,8-dimethyl-4-nonanone

A 10 mL one neck round bottom flask, fitted with argon inlet, magnetic stirrer, and reflux condenser was charged with 1.0 mL glacial acetic acid, 4 drops of concentrated HCl and 200 mg(0.81 mM) of 2,3,4,5-tetrahydro-2-oxo-3-(5,5-dimethyl-2,2-difluoro-1-oxohexyl)furan. The reaction mixture was heated at 110 C. overnight under a blanket of argon. The reaction was extracted with ethyl ether, and the ether was cross washed with water, dried (anhydrous MgSO4), and solvent removed under reduced pressure. The residue was chromatographed on a 10×60 mm silica gel column using a 9:1 hexane:ethyl acetate mixture to give a clear oil. nmr(CDCl₃) -L 0.95(s,9H), 1.45(t,2H), 2.00(m,6H), 3.12(bs,1H), 4.15(m,1H)

EXAMPLE III

N,N-dimethyl-N-[2-(hydroxy)ethyl]-5,5,5-trifluoro-4-oxopentanaminium, hydroxide salt

A.
2,3,4,5-Tetrahydro-2-oxo-3-[(2,2,2-tri-fluoro-1,1-dihydroxy)ethyl]furan

A 3L three neck round bottom flask, fitted with reflux condenser, dropping funnel, argon inlet, magnetic stirrer, and heating mantle was charged with 36 g(0.75M) of a 50% oil dispersion of sodium hydride. The sodium hydride was washed (2×200 mL) with dry hexane and then suspended in 800 mL of ethyl ether and 2 mL of absolute ethanol. A mixture of 60.2 g(0.7M) of γ-butyrolactone and 99.4 g(0.7M) of ethyl trifluoroacetate in 750 mL of ether was added to the suspension at a rate to keep the reaction at gentle reflux. The mixture was refluxed for an additional two hours and then stirred at ambient temperature overnight. The reaction was cooled in an ice bath and 1N HCl (250 mL) was added. The organic layer was separated, washed with water (2×200 mL), dried (anhydrous MgSO4), and solvent removed under reduced pressure. The residue was crystallized from hexane:ethyl acetate to give 64.0 g (45.4%), mp- 87–90

C. nmr(DMSO-d6) -L 2.33(m,2H), 3.09(t,1H)J=7Hz, 4.20(m,2h), 7.00(s,1H), 7.52(s,1H).

B. Preparation of 1,1,1-trifluoro-5-hydroxy-2-pentanone

A 500 mL three neck round bottom flask, fitted with reflux condenser, heating mantle, and magnetic stirrer was charged with 61.5 g(0.31M) of 2,3,4,5-tetrahydro-2-oxo-3-(2,2,2-trifluoro-1,1-dihydroxyethyl)furan, 6.4 mL of concentrated HCl, 10 mL of water, and 80 mL of acetic acid. The reaction mixture was heated at 125 C. overnight. An additional 3.0 mL of concentrated HCl and 5.0 mL of water was added and the reaction mixture was heated for an additional 10 hour. The reaction was partitioned between water and ethyl ether while the water layer was neutralized with solid sodium bicarbonate (100 g). The ether solution was washed with water (2×20 mL), dried (anhydrous MgSO4), and solvent removed under reduced pressure to give 60 g(45%) of a pale yellow oil. nmr(CDCl₃)-L 2.15m,4H), 4.03(m,1H), 4.20(m,1H).

C. 1,1,1-Trifluoro-5-bromo-2-pentanone

A 500 mL three neck round bottom flask, fitted with dropping funnel, magnetic stirrer, ice-salt bath, and argon inlet is charged with 125 mL of dry dimethylfofmamide, 29 g(35.7 mM) of tributyl phosphine, and 11.2 g(54.9 mM) of 1,1,1-trifluoro-5-hydroxy-2-pentanone. This mixture was cooled to −5 C. and 11.5 g(71.6 mM) of bromine was added dropwise over a 2 hour period. After stirring overnight at ambient temperature the reaction-mixture was distilled though a 30 cm vigreaux column at 2.0 mm of pressure. Two fractions were collected; the first fraction from 27–35 C. and the second fraction at 35–70 C. The second fraction was partitioned between water and ethyl ether, the organic layer was washed with water (3×100 mL), dried (anhydrous MgSO4), and evaporated under reduced pressure at ambient temperature to give 30 g of a colorless oily mixture of dimethyl formamide, ether, and the desired product which was used in the next reaction without further purification.

D. N,N-dimethyl-5,5,5-trifluoro-4-oxopentanamine

A 500 mL three neck round bottom flask, fitted with dropping funnel, argon inlet, magnetic stirrer, and ice-salt bath was charged with 21.5 g(0.45M) of anhydrous dimethylamine at −8 C. To this mixture was added 19.4 g(88.5 mM) of 1,1,1-trifluoro-5-bromo-2-pentanone in dimethyl formamide and ethyl ether dropwise at −10 C. The suspension was stirred for 2.5 hours at −10 C. The solvent was then decanted from the precipitate. The precipitate was washed with ethyl ether (3×200 mL), the organic layers were combined, washed with water (2×30 mL), dried (anhydrous MgSO4), and evaporated under reduced pressure to give 15.0 g(92%) of a pale yellow oil. nmr of HCl salt (CDCL₃) - 1.89(s,4H), 2.90(s,6H), 3.21(t,2H).

E.
N,N-dimethyl-N-[2-(methoxy)ethyl]-5,5,5-trifluoro-4-oxopentanaminium, hydroxide salt A 25 mL one neck round bottom flask was charged with 2.95 g (21.2 mM) of 2-bromoethyl methyl ether, 0.33 g(1.77 mM) of N,N-dimethyl-5,5,5-trifuluoro-4-oxopentanamine) and 2.5 mL of dimethyl formamide and the mixture was stirred at ambient temperature for 3 days. Solvent was removed under reduced pressure and the amber oil was chromatographed on a Dowex-1 (15×200 mm) column in the hydroxide form with 200 mL of water. The effluent from the column was lyophilized to yield 0.28 g(60%) of an amber oil which was the as the hydroxide salt. nmr(D₂O)-product 1.94(m,2H), 3.13(s,6H), 3.39(s,3H), 3.41(m,2H), 3.60(m,2H), 3.88(bs,2H). The material was used in next reaction without further purification.

F.
N,N-dimethyl-N-[2-(hydroxy)ethyl]-5,5,5-trifluoro-4-oxopentanaminium, hydroxide salt A 10 mL round bottom flask, fitted with argon inlet and reflux condenser was charged with 0.275 g(1.1 mM) of N,N-dimethyl-N-[2-(methoxy)ethyl]-5,5,5-trifluoro-4-oxopentanaminium, hydroxide salt, 4.0 mL of water and 8.0 mL of 30% HBr in acetic acid. This mixture was heated at 120 C. for five hours, cooled, and the solvent removed under reduced pressure. The residue was co-evaporated with 3×20 mL of water and the resulting oil was chromatographed on a Dowex-1 (15×200 mm) column in the hydroxide form. Evaporation of the effluent under reduced pressure gave 0.17 g(63%) of the product as the hydroxide salt. nmr(D₂O)- 1.90(m,4H), 3.13(s,6H), 3.30(m,2H), 3.48(m,2H), 4.01(bs,2H).

EXAMPLE IV

N,N-dimethyl-N-[2-(phosphonooxy)ethyl]-5,5,5-trifluoro-4-oxopentanaminium, ammonium salt A 10 mL three neck round bottom flask fitted with dropping funnel, argon inlet, magnetic stirrer, and ice salt bath is charged with 0.093 mL(1.0 mM) of phosphorus oxychloride and 0.5 mL of trimethyl phosphate. To this mixture was added 70.0 mg(0.2 mM) of N,N-dimethyl-N-[2-(hydroxy)ethyl]-5,5,5-trifluoro-4-oxopentanaminium, hydroxide salt dropwise at −10 C.

The mixture was stirred for 30 minutes and then placed in a freezer overnight. The mixture was triturated with ethyl ether followed by petroleum ether (4×50 mL) to give a resinous precipitate. This precipitate was covered with ice, neutralized to pH 6.0 with 1N NaOH, and evaporated to dryness under reduced pressure. The resulting solid, 107 mg, was dissolved in 30 mM NH4OAc buffer at pH 7.0 and purified by HPLC with system B. The product, which eluted at 12 minutes, was isolated by lyophilization of the buffer to give 9.0 mg(11%) of a colorless resin. nmr($D_2O$)- L 1.90(m,4H), 3.14(s,6H), 3.42(m,2H), 3.60(m,2H), 4.19(bs,2H).

EXAMPLE V

Half Sandwich Assay for Hexon Antigen from Adenovirus

General Procedure

Two-fold serial dilutions of purified Adenovirus hexon protein were coated onto a polyvinyl microtiter plate in pH 9.5 carbonate buffer (10 mM) for a period of 1-18 hours. The plate was rinsed several times with a solution consisting of 0.05% polyoxyethylenesorbitan monolaurate in phosphate buffered saline. The immunological reaction was performed using an antibody (mouse-anti-hexon IgG) conjugated to alkaline phosphatase diluted to an appropriate level in 10% culture medium (containing fetal calf serum). After incubation for 1 hour, and a standard rinse procedure, a mixture of blocked modulator (10-3-10-4M) and RLE (10-8-10-9M) was added, -and the plate was preincubated for 10 to 60 minutes. A chromogenic substrate (i.e. indoxyl butyrate or o-nitrophenyl butyrate) was added to the mixture. Color development typically occured within 15 minutes, and could be stabilized for a longer period of time by the addition of excess free modulator. Wells which were coated with dilutions containing 1 ng/mL of hexon protein gave a positive response with this system.

EXAMPLE VI

Sandwich Assay for Adenovirus

A polyvinyl chloride microtiter plate was coated with anit-adenovirus antibody by incubating the plate for 1 hour at 37° C. in a 1:900 dilution of 4.5 mg/mL stock solution of the antibody in a 10 mM carbonate 20 mM ethylenediaminetetraacetic acid (EDTA) buffer. The plate was washed 3 times with a wash buffer solution consisting of 0.5% casein in 10 mM TRIS and 154 mM NaCl at pH 7.6. Adenovirus infected HeLa cells diluted to ca $1 \times 10^5$ plaque forming units (PFU)/ml in pH 7.4 phosphate buffered-saline containing 0.05% polyoxyethylenesorbitan monolaurate, 0.1 mg/ML gentamicin, 0.5% phenol red, 0.1% bovine serum albumin, 10 mM EDTA and 100 mM ethylene bis(oxyethylenenitrilo) tetraacetic acid were serially diluted in 2-fold steps across the plate. The plate was incubated-as above to bind the cells to the antibody, washed with wash buffer, incubated with a 0.005 mg/mL tracer solution of anti-adenovirus conjugated to alkaline phosphatase in wash buffer containing 0.5% gelatin and 10% inactivated fetal calf serum. Excess tracer solution was decanted and the plate was washed 3 times with TRIS buffer (without casein). A mixture of a $1 \times 10^{-4}$M solution of the blocked inhibitor from Example I and $5 \times 10^{-9}$M RLE in 50 mM TRIS buffer, pH 8.5, was added and the plate was incubated at room temperature for 10 minutes. o-Nitrophenyl butyrate (1 mM) was then added to each well of the plate.

Control wells having no antigen typically showed color detectable with the naked eye in ca 15 minutes, and addition of free inhibitor (product B from Example I) to the control wells inhibited color formation for longer periods. Test wells having antigen dilutions remained colorless for periods of time in excess of 15 minutes.

The FIGURE shows the relationship of color formation to antigen concentration as determined with a Beckman DU7 spectrophotometer 20 minutes after chromogen addition. It is seen that the optical density (OD) of the solution in the control wells is substantially constant at about 0.24, and that the OD of the solutions in the test wells is inversely proportional to antigen concentration and approaches the control value at very low antigen concentrations.

In summary, the invention provides a method for detection or determination of a ligand present in a liquid sample at very low levels. After binding the ligand, antiligand and tracer, the bound phase is separated and contacted with a second enzyme and a blocked modulator whereby a first enzyme component of the tracer removes the blocking group to provide a modulator for the second enzyme. The resulting modulator affects conversion of a substrate to a product by the second enzyme leading to a detectable signal. Detection of the signal establishes the presence or absence of the ligand in the sample. By measuring the magnitude of the signal, the concentration of the ligand may be determined. The modulator and the second enzyme provide two amplification stages whereby the signal is amplified by $10^6$ fold or more, enabling naked eye detection of the signal in a time up to 100 fold less than by conventional EIA.

What is claimed is:

1. A blocked enzyme inhibitor selected from the group of fluoroketones consisting of the general formulas I, II, III and IV

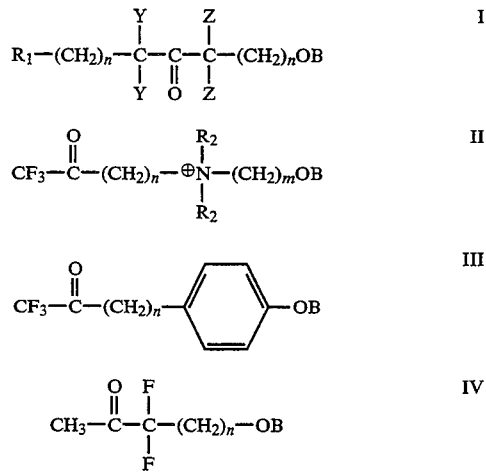

wherein $R_1$ is t-butyl or

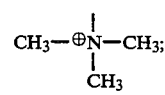

$R_2$ is lower alkyl of 1-6 carbon atoms, Y and Z are independently H of F wherein at least one of Y and Z is F; m is 2 to 3; n is 1-31 and B is an enzymatically hydrolysable group selected from the group consisting of a glycosyl group hydrolysable by a glycosidase, an acyl group of 2-4 carbon atoms hydrolysable by an esterase and a phosphoric acid, ester or salt thereof of the structure

hydrolysable by alkaline phosphatase.

2. A blocked enzyme inhibitor of the formula

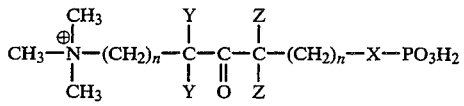

where Y and Z are independently H or F wherein at least one of Y and Z are F; X is O or S; and n is 1-4.

3. A blocked enzyme inhibitor of the formula

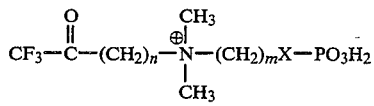

wherein n is 1-4; m is 2-4; and X is O or S.

* * * * *